United States Patent [19]

Li et al.

[11] Patent Number: 5,168,104
[45] Date of Patent: Dec. 1, 1992

[54] MACROPOROUS PARTICLES AS BIOCOMPATIBLE CHROMATOGRAPHIC SUPPORTS

[75] Inventors: Nai-Hong Li; M. Abdul Mazid, both of Edmonton, Canada

[73] Assignee: Chembiomed, Ltd., Edmonton, Canada

[21] Appl. No.: 759,576

[22] Filed: Sep. 13, 1991

[51] Int. Cl.⁵ .............................. C08J 9/10; C08J 9/26; C08J 9/32
[52] U.S. Cl. ........................................ 521/64; 521/91; 521/92; 521/95; 521/96; 521/122; 521/123; 521/141; 521/146; 521/147; 521/149; 521/150; 521/61; 523/218; 523/219
[58] Field of Search ................... 521/91, 92, 95, 96, 521/122, 123, 141, 146, 147, 149, 150; 523/218, 219

[56] References Cited

U.S. PATENT DOCUMENTS

| | | | |
|---|---|---|---|
| 2,514,141 | 7/1950 | Phillips | 521/138 |
| 4,104,209 | 8/1978 | Mikes et al. | 521/63 |
| 4,224,415 | 9/1980 | Meitzner et al. | 521/38 |
| 4,256,840 | 3/1981 | Meitzner et al. | 521/33 |
| 4,263,268 | 4/1981 | Knox et al. | 264/29.1 |
| 4,297,220 | 10/1981 | Meitzner et al. | 210/690 |
| 4,382,124 | 5/1983 | Meitzner et al. | 521/38 |
| 4,430,451 | 2/1984 | Young et al. | 521/64 |
| 4,933,372 | 6/1990 | Feibush et al. | 521/91 |
| 4,966,919 | 10/1990 | Williams Jr. et al. | 521/54 |
| 4,980,004 | 12/1990 | Hill | 521/54 |
| 4,980,102 | 12/1990 | Hill | 521/54 |
| 5,037,859 | 8/1991 | Williams Jr. et al. | 521/54 |

FOREIGN PATENT DOCUMENTS 0370259 5/1990 European Pat. Off. .

OTHER PUBLICATIONS

Menger et al., *J. Amer. Chem. Soc.* (1990) 112:1263-1264.

Primary Examiner—Morton Foelak
Attorney, Agent, or Firm—Morrison & Foerster

[57] ABSTRACT

A method to prepare uniform populations of macroscopic beads containing pores of at least 0.1 microns diameter is described. The beads consist essentially of a copolymer of a monoethylenically unsaturated monomer and a crosslinking polyethylenically unsaturated monomer, said resulting copolymer optionally being derivatized with functional groups, linking moieties, and/or affinity ligands. The macroporous beads are obtained by utilizing, as porogen in the polymerization reaction, porous inorganic particles which have been preabsorbed with a blowing agent. The blowing agent is not activated until after the polymerization takes place; when the blowing agent is activated, the organic polymer which isolates the inorganic porogen particles from each other in the bead is destroyed. Upon subsequent dissolution of the inorganic porogen, a network of pores throughout the organic copolymer-formed particle is formed. The resulting beads are useful in a variety of chromatographic, analytical and biomedical techniques.

7 Claims, No Drawings

MACROPOROUS PARTICLES AS BIOCOMPATIBLE CHROMATOGRAPHIC SUPPORTS

TECHNICAL FIELD

The invention relates to macro- and megaporous polymer beads and to their use as supports in connection with immunoadsorptin, chromatography, and immobilization of biological molecules. Specifically, the invention concerns a process for preparation of such porous particles which results in macroscopic particles with large-size pores.

BACKGROUND ART

Particulate supports used in separation processes, especially those involving biological materials, are advantageously characterized by the properties of being derivatizable to desired affinity ligands and ability to permit the free flow of fluids which may contain macromolecules and/or particles that desirably are not retarded mechanically by the support. Thus, the solid support should be capable of providing surface functional groups which can be used to link the support to the desired ligand. The support should also have a sufficient surface area to provide a high concentration of said ligands, but should provide passages for fluids which do not either retard contaminants or, worse, preclude access of the substance desired to be absorbed to the affinity ligand to the position of the ligand on the support. Thus, if the surface area is achieved by supplying particles containing pores, the pores must be of sufficient size to accommodate the contents of the fluid to be treated.

Because the above characteristics are most easily achieved by using rigid spherical particles of adequate size to provide reasonable flow rates, adequate surface area is best achieved by insuring that these particles are porous. The surface of the pores may then be employed to accommodate the affinity ligands. Preparation of such porous, rigid, and spherical solid supports have utilized several approaches.

In one approach, polymerization is conducted in a suspension, but in the presence of one or more agents designed to generate pores in the polymerized, finished product. This approach is described in U.S. Pat. Nos. 4,224,415; 4,256,840; 4,297,220; and 4,382,124. Soluble polymers have been used to function as porogens as described in U.S. Pat. No. 4,104,209. Reverse micellular systems obtained by adding water and suitable surfactant to a polymerizable monomer have been described as porogens by Menger et al., *J Am Chem Soc* (1990) 112:1263–1264.

Alternative approaches have used thermal induction of phase separation to generate porous substances as described in European Patent Application 370,259 or U.S. Pat. No. 4,430,451.

More closely related to the approach of the present invention is the application of template polymerization. This procedure, described, for example, in U.S. Pat. No. 4,263,268 and U.S. Pat. No. 4,933,372, relies on the use of an inorganic porous particle as a template, in the pores of which the desired organic polymer is polymerized. When the inorganic template is removed (by dissolution in an appropriate solvent) the remaining organic particles are formed in the image of the pore structure of the inorganic support. The pores resulting in these particles are relatively small as they relate to the dimensions of the nonporous substance of the template particles and the size of the individual particles is governed by the size of the individual inorganic templates.

The method of the present invention overcomes these difficulties by providing a means to obtain particles of larger dimensions and having pores of greater diameter, nevertheless networked throughout the particle. Disclosure of the Invention The invention provides large, rigid macroporous polymer beads wherein the pore size is generally larger than one micron in diameter. The results beads are of sufficient size and of sufficient pore size to permit ready flow of liquids through them, and to accommodate high densities of affinity ligands coupled to the surface external to the particles and internal to the pores. These macroscopic particles are obtained by first filling the pores of inorganic porous particles with a "blowing agent"—a temporary filler which will be moved at the end of the preparation. The inorganic particles, with pores blocked, are then used per se to create the internal pores in a macroparticle formed around a collection of such inorganic particles. After polymerization of the organic component to obtain the macroparticles, the blowing agent is activated to liberate the pores and to disrupt that portion of the polymerized materials which separates the inorganic particles. Thus, channels are created which connect the inorganic particles and the high-diameter pores are then formed throughout the polymer bead as the template particles are removed.

Thus, in one aspect, the invention is directed to a composition which comprises macroscopic beads of crosslinked organic polymer which are permeated by megapores. These particles may further be derivatized to contain, at the surfaces of the pore and of the exterior, functional groups which permit covalent binding of coupling agents or affinity ligands to the surfaces. The particles may further contain ligands thus coupled. These beads are useful in a variety of applications wherein separation, analysis, alterations of concentration, and the like are desired.

Thus, in other aspects, the invention relates to methods to conduct separation or analysis using the beads of the invention. The invention further includes devices or containers configured so as to accommodate the invention beads and containing these beads. In still another aspect, the invention is directed to methods to prepare the macroscopic beads.

MODES OF CARRYING OUT THE INVENTION

The invention is directed to a process for preparation of organic polymer beads which are suitable as supports for a variety of ligands. The derivatized beads are useful in a wide range of scientific, biomedical, analytical, and industrial applications. The compositions of the invention comprise beads which are rigid, roughly spherical particles of macroscopic dimensions that contain networks of pores having diameters of at least 0.1 microns, preferably at least 0.5 microns. It is recognized that complete uniformity of pore size cannot be readily achieved, and thus, by the statement that the beads contain networks of pores of 10 this diameter is meant that at least 90% of the pore diameter contained in the beads is of at least the stated dimension. Thus, if one were to survey the entire pore network in the particle preparation, at 90% of the locations surveyed, the minimum diameter would be met.

The pore size is basically determined by the size of inorganic porous particles used as porogens in the polymerization mixture. The diameter of the pores will approximate in size of these inorganic particles. The inorganic particles are removed after the polymerization process has occurred, and, as explained below, the presence of a blowing agent in the porous inorganic particles insures that a network is formed between the inorganic porogen particles in the bead.

In general, the polymerization reaction is carried out using the monomers destined to form the copolymer in a suspension which contains the appropriately sized porous inorganic particles. Of course, a polymer is not formed in the space occupied by the inorganic matter. In prior art methods of using such inorganic particles as porogens, the organic monomers were allowed to flow into the pores of the particles and to polymerize therein. Thus, when the inorganic particles are dissolved away, there was obtained a series of small organic beads of the approximate dimension of the inorganic particles, and having a network of pores which is an image of that of the porous inorganic particles.

For example, the above-referenced U.S. Pat. No. 4,933,372 describes such a process where the porous rigid resins obtained are said to "mirror the size, surface area, and porosity of the template particles" (column 2, lines 53-55).

In the invention process, however, the pores of the inorganic particles are filled with a "blowing agent" which is a substance capable of being decomposed under appropriate conditions. As the pores of the inorganic particles are filled during the polymerization reaction, the organic polymer which forms the beads surrounds, rather than penetrates, the inorganic particles. After the polymerization is completed, organic, roughly spherical beads are formed containing a multiplicity of the inorganic porogens within their volumes. The inorganic particles will, however, be insulated from each other by a small amount of organic polymer which surrounds the inorganic particles. The blowing agent is then activated, causing the organic polymer in the immediate vicinity of the inorganic particle to be destroyed. This results in the formation of channels between the inorganic particles, facilitating the dissolution of these inorganic particles in an appropriate solvent, and creating a network of channels through the organic bead.

The organic copolymer which forms the bead compositions of the invention will be derived from at least one monounsaturated (monoethylenic) monomer and at least one polyunsaturated (polyethylenic) monomer. Suitable monounsaturated monomers include, for example, acrylic and methacrylic esters, typically esterified with substituted or unsubstituted hydrocarbyl residues of 1-6C; styrene, styrene/containing substitutions in the phenyl residue, said substitutions generally including, for example, halo, halomethyl, alkoxy (1-6C) and the like; and vinyl alcohol or esters thereof such as vinyl acetate, vinyl propionate, vinylhexanoate and the like.

Suitable polyunsaturated monomers include those listed in U.S. Pat. No. 4,933,372, incorporated herein by reference. Preferred among these are divinyl benzene, triallyl isocyanurate, and pentaerythritol trimethylacrylate.

The inorganic porous particles useful as porogens include minerals and refractory materials such as glassy forms of silica, alumina or zirconia. As the pore size is determined by the size of the inorganic particles, it is helpful to utilize particle preparations which are of uniform diameter.

Of course, mixtures of inorganic particles of different compositions can be used, and in any event, the inorganic porogen does not appear in the final product. Similarly, mixtures of the monounsaturated and/or polyunsaturated monomers can be used to obtain mixed copolymers.

The polymerization may be initiated by any means convenient in the art. Various initiators may be used to induce the start of the polymerization reaction, which is conducted at a temperature suitable for the reaction conditions in a particular setting. If the blowing agent is activated at a high temperature, the temperature of the polymerization reaction must be below that of the activation.

In general, the same types of compounds can be used as initiators and as blowing agents. These are peroxy compounds, such as benzoyl peroxide, peroxyesters and azo compounds such as azo-bis-isobutyronitrile. The amount of initiator needed is generally about 0.1-2% of the weight of the monomers; the amount of the blowing agent is selected so as to provide an amount which just fills the pores of the inorganic porous particles. For example, for particles of 0.6 ml/g pore volume, approximately 0.6 ml of liquid blowing agent is used per gram of inorganic particles. The inorganic particles are preabsorbed with the relevant amount of blowing agent prior to mixing them into the polymerization suspension.

As used herein, the blowing agent in the "inert" state refers to a composition of the blowing agent which has not decomposed. The blowing agent in the "activated" state refers to conditions wherein decomposition of the blowing agent occurs and disruption of the surrounding organic polymer is effected.

Thus, in the method of the invention, the selected porous inorganic particles are first treated with a volume of blowing agent which is approximately equivalent to the pore volume of the particles employed. Appropriate blowing agents include peroxides, such as isopropyl peroxy dicarbonate, lauryl peroxide, benzoyl peroxide, t-butyl peroxybenzoate, and also includes azo nitriles such as 1,1'-azo-bis(cyanocyclohexane)nitrile, 2,2'-azo-bis(2-methyl butyronitrile) and the like. In general, the blowing agent is selected so as to have a higher thermal decomposition temperature than the initiator that will be used.

For example, if the initiator is 2,2'-azo-bisisobutyronitrile, this can effectively be used in combination with t-butyl peroxybenzoate. In this instance, polymerization can be initiated at about 55° C. and the reaction system maintained at 70°-75° C. for 3 hrs to effect polymerization. The temperature is then raised to about 90° C. to decompose the blowing agent. The temperatures and times at which the polymerization is conducted and the conditions to effect activation of the blowing agent depend, of course, on the choice of the initiator, the nature of the monomers, the nature of the inorganic particles, and the nature of the blowing agent. Manipulation of these parameters in respect of these materials is well understood in the art.

After the polymerization is conducted for a suitable time and at a suitable temperature, the blowing agent is activated to effect disruption of the wall formed by the organic polymer between the inorganic particles in the polymeric bead. When this wall has been disrupted, the inorganic particles are removed by use of a suitable solvent. A choice of solvent will depend on the nature of the inorganic particles; for example, for silica particles, strong basic aqueous solutions can be used. The solvent is conveniently chosen so as to dissolve only the inorganic particles leaving the porous organic polymeric bead behind.

The organic polymeric bead formed typically is of at least 1 micron in diameter and contains proportional diameter pores forming a network. As set forth above, approximately 90% of the pore diameter is at least 0.1 microns; preferably 0.5 microns, and most preferably 1 micron in the event that larger beads are formed.

The polymer bead itself may contain functional groups capable of coupling to linking agents and/or ligands which are useful in separations or catalysis. In the event that the polymer itself does not contain such functional groups, suitable derivatization can be effected to provide them. For example, in the case of formation of the copolymer of styrene and divinyl benzene, the polymeric beads can be chloromethylated and hydrolyzed to provide hydroxyl functional groups. Other polymers, such as those obtained from vinyl esters which are hydrolyzed to vinyl alcohol contain functional groups that are already resident in the polymer.

The functional groups can then be linked to suitable reagents; for example, the hydroxyl groups can be reacted with epoxy or silanizing agents to obtain matrices which can be further reacted with enzymes, antibodies, receptor ligands, haptens, and the like.

The derivatized beads of the invention then find a variety of uses depending on the nature of the ligand. For example, compositions of beads coupled to affinity ligands can be used in chromatographic separations or in analytical techniques. Such affinity ligands can include antibodies, antigens, haptens, receptors, receptor ligands, or fragments thereof. The beads coupled with enzymes are conveniently used in catalysis of enzyme-mediated reactions, thus providing a convenient source of immobilized enzymes.

Because the bead compositions of the invention are quite porous, even large target molecules such as IgM antibodies can be adsorbed from solutions.

In addition, because the flow rates are favorable, the fluids applied and flowed through containers which contain the bead compositions of the invention can themselves be relatively viscous. For example, materials may be separated or analyzed in blood, or blood may be treated with the beads to alter its composition.

The following examples are intended to illustrate but not to limit the invention:

EXAMPLE 1

A. Preparation of ST/DVB Beads

Into a three-necked round-bottomed flask (500 mL) equipped with a reflux condenser, a nitrogen inlet tube and a stirrer, containing 1.0 g of polyvinyl alcohol in 100 mL of water, was charged a homogeneous mixture divinylbenzene (DVB, 80% purity), 100 mg of 2,2'-azo-bis-isobutyronitrile, and 3.0 g of porous silica bead (5 μm particle size, 0.6 mL/g pore volume, 100 Å average pore diameter) preabsorbed with 1.8 mL of t-butyl peroxybenzoate, and the resulting mixture was stirred. The mixture was heated at 65° C. for 3 min, then to 70°–75° C. for 3 h and 90° C. for another 3 h while stirring to effect suspension polymerization. A spherical copolymer bead was obtained. The copolymer was filtered, washed with water, methanol, dichloromethane and acetone so that the residual monomer and initiator were extracted.

The polymer bead together with a solution of 65 g of sodium hydroxide in 200 mL of water was placed into a 500 mL Parr bottle. This was agitated at room temperature for 20 h to dissolve the silica particles. The resulting polymer beads were filtered, washed with water and dried under vacuum at 60° C.

Samples of the bead were burnt at a temperature of ~1000° C. which showed that more than 95% of the silica was removed by the treatment with sodium hydroxide.

B. Derivatization of ST/DVB Beads

Ten g of the polymer bead was charged into a 100 mL round-bottomed flask with a well-sealed rubber stopper. Further, 50 mL of chloroform and 15 mL of chloromethylethyl ether were charged into the flask. The suspension was agitated for 30 min at room temperature and 2 mL of anhydrous stannic chloride was added while agitating. A gradual change in color, white to yellow, was observed. After completing the addition of stannic chloride, the reaction was allowed to proceed for 4 h at room temperature with constant agitation. The beads were then filtered and washed extensively with methanol, chloroform, dioxane-water (3:1), dioxane-3N HCl (3:1), dioxane, dioxane-water (3:1), water and finally methanol. After drying under vacuum at 60° C., the chloromethylated poly(ST/DVB) bead was hydrolysed with strong alkali. The resulting —CH$_2$OH functional groups permit derivatization to obtain beads coupled to affinity ligands, as described below. The properties of the porous copolymer bead are given in Table I.

EXAMPLE 2

Example 1A was repeated in all respects except that vinylbenzyl chloride (VBC) was substituted for styrene. The poly(vinylbenzyl chloride-divinylbenzene), i.e., poly(VBC/DVB) beads hydrolyzed with strong alkali to provide —CH$_2$OH functional groups, and derivatized to affinity ligand as described below. The properties of the porous copolymer bead are set forth in Table I.

EXAMPLE 3

Example 1A was repeated in all respects except that 2-hydroxyethyl methacrylate (HEMA) was substituted for styrene. The polymer bead prepared was designated poly(HEMA/DVB). This bead was used as described in Examples 11 and 13 below.

EXAMPLE 4

Example 1A was repeated in all respects except that 2-hydroxyethyl methacrylate (HEMA) and pentaerythritol trimethacrylate (PTMA) were used as monomer and cross-linker, respectively, and the polymer was designated poly(HEMA/PTMA). FIG. 1 shows the scanning electron micrograph of the porous resulting copolymer bead, and its properties are set forth in Table I below. The bead was used as described in Examples 11 and 12 below.

EXAMPLE 5

Example 1A was repeated in all respects except that 2-hydroxyethyl methacrylate (HEMA) and ethylene glycol dimethacrylate (EGDM) were used as the monomer and cross-linker, respectively. The polymer bead prepared was designated poly(HEMA/EGDM).

EXAMPLE 6

Example 1A was repeated in all respects except that glycidyl methacrylate (GMA) and triallylisocyanurate (TAIC) were used as the monomer and cross-linker, respectively, to obtain poly(GMA/TAIC).

EXAMPLE 7

Example 1A was repeated in all respects except that pentaerythritol trimethacrylate was substituted for the triallylisocyanurate as the cross-linker, and poly(GMA/PTMA) was obtained.

EXAMPLE 8

Example 1A was repeated in all respects except that 6.64 g of styrene was replaced by 7.45 g of vinyl propionate as the monomer and 5.0 g of the same silica bead was used as the porogen. The silica particle was subsequently removed by treatment of the polymer bead with a solution of 65 g of sodium hydroxide in a mixture of 100 mL of water and 100 mL of methanol in a Parr bottle. In this procedure, the ester group of the vinyl propionate was hydrolyzed to vinyl alcohol (VA) at the same time, and a poly(VA/DVB) bead was obtained. FIG. 2 shows the scanning electron micrograph of the porous copolymer bead, and its properties are set forth in Table I below.

EXAMPLE 9

Example 8 was repeated in all respects except that vinyl acetate replaced vinyl propionate, and a poly(vinyl alcohol/DVB) bead was obtained.

EXAMPLE 10

Example 8 was repeated in all respects except that triallylisocyanurate was used instead of divinylbenzene as the cross-linker to obtain a poly(VA/TAIC) bead.

The properties of the beads prepared in Examples 1, 2, 4 and 8 are as follows:

TABLE I

Characteristics of Porous Copolymer Beads Prepared by Different Examples

| Example Number | Polymer Bead Designation/Composition | | Pore Volume (mL/g) | Density (g/mL) | % Weight Loss after Burning |
|---|---|---|---|---|---|
| 1$^a$ | DV1-104 | ST/DVB | 0.77 | 0.57 | 98.7 |
| 1$^b$ | DV2-5 | ST/DVB | 1.71 | 0.32 | 98.8 |
| 2$^a$ | DV2-4 | VBC/DVB | 1.37 | 0.19 | 100 |
| 4$^a$ | DV1-116 | HEMA/PTMA | 0.53 | 0.72 | 99.6 |
| 4$^a$ | DV1-118 | HEMA/PTMA | 0.63 | 0.62 | 100 |
| 4$^b$ | DV2-6 | HEMA/PTMA | 1.50 | 0.39 | — |
| 4$^b$ | DV2-24 | HEMA/PTMA | 1.02 | 0.50 | 100 |
| 8$^a$ | DV1-96 | PVA/DVB | 1.37 | 0.48 | 95.0 |

$^a$Diameter of the porogenic silica particle used in the Example was 5 μm. and the average pore diameter of the resulting copolymer bead prepared was approximately 4–8 μm, as estimated from scanning electron micrographs (SEM).
$^b$Particle diameter of the porogenic silica was approximately 0.5–2 μm. and the resulting copolymer bead had an estimed pore diameter of 0.50–2 μm from SEM.

EXAMPLE 11

Preparation of Immunoadsorbents with Synthetic Oligosaccharide Hapten Representing Human Blood-Group A Substances Coupled to Porous Polymer Beads A. The hydroxyl-group-containing polymer beads prepared in Examples 1–4 and 8 above were utilized for chemical coupling of a spacer-linked blood-group A-trisaccharide ($\alpha$GalNAc(1→3)[$\alpha$Fuc(1→2)] $\beta$Gal-O(CH$_2$)$_8$COOH), following initial activation and functionalization of the bead by suitable modification of literature procedures, as described recently by Mazid, M. A., et al. (*Bioconjug Chem* (1991) 2:32–37). In general, 250 mg of the polymer bead was suspended in 3 mL solution of 0.4 M NaOH containing 20% dioxane and 0.3 mL of epichlorohydrin. This was mixed overnight at room temperature (21° C.), followed by washing the polymer bead with the solvent and then thoroughly with water. The epoxide group was opened by reaction with neat ethhlenediamine at 40° C. for 2 h after which the polymer bead was washed well again with water.

B. Coupling of the carboxyl-terminated A-trisaccharide hapten to the amino-derivatized polymer bead was carried out using aliquots of the A-trisaccharide acid activated with an excess of molar equivalent of di-N-succinimidyl carbonate in a small volume of dimethylformamide (0.2–0.5 mL). The activation of the hapten was carried out for 2–3 h, whereas the coupling reaction was continued overnight (12–16 h), both at room temperature with gentle mixing. The haptenated polymer bead (hereinafter called immunoadsorbent) was washed thoroughly with water, the washings being saved for the estimation of the A-trisaccharide, and therefore its incorporation in the bead, by the phenol-sulfuric acid assay of Dubois, M., et al. (*Anal Chem* (1956) 28:350–356). Finally, after washing with methanol, the remaining amino groups in the beads were blocked by acetylation with 5% acetic anhydride in methanol. When not in use, the immunoadsorbent was dried from methanol and stored in a glass vial at room temperature.

The hapten incorporations of these immuno-adsorbents as well as their bioactivities, as demonstrated in Example 12, are given in Table II below.

TABLE II

Biological Activity of Polymer Beads Coupled with A-Trisaccharide

| Example Number | Polymer Bead Designation | Hapten Incorporated (μmole/g) | Human A$_1$ Titers anti-A IgM* |
|---|---|---|---|
| 1 | DV2-5 | 0.47 | 256 |
| 2 | DV1-110(4) | 0.32 | 256 |
| 3 | DV1-134 | 9.6 | 512 |
| 4 | DV2-6 | 0.93 | 128 |
| 4 | DV1-116 | 3.27 | 128 |
| 4 | DV1-118 | 0.9 | 128 |
| 4 | DV2-23 | 0.2 | 128 |
| 8 | DV1-110(1) | 2.1 | 128 |
| 8 | DV1-102 | 1.95 | 256 |

*The initial anti-A IgM titer before immunoadsorption of the O-plasma was 1024.

EXAMPLE 12

Biological Activity of Immunoadsorbents Prepared by Using Different Polymer Beads The immunoadsorbents prepared with various polymer beads of the present invention were tested for their biological activity by an in vitro hemagglutination technique. In this procedure, 25 mg of the immunoadsorbent bead (methanol-dried) was incubated with 0.5 mL of human 0-plasma by end-over-end rotation on a hematology mixer for 2 h at room temperature (21° C.). The supernatant was then removed, and anti-A antibody titers of IgM were determined by saline agglutination test at 37° C. from serial dilutions using standard procedures with human A$_1$ red blood cells (A$_1$RBC), as described recently by Mazid et al., supra. The antibody titers are expressed as the reciprocal of the highest dilution of plasma that produces macroscopically visible agglutination of RBC. The bioactivity of the immunoadsorbents together with their hapten incorporations are summarized in Table II. The results indicate that the polymer beads used in the preparation of the immunoadsorbents have sufficiently large pores (at least ca. 0.1 μm) to permit interaction between the coupled hapten and the large IgM molecule which has a molecular weight of 970,000 Da (*Dictionary of Immunology*, 3d ed. (W. J. Herbert et al., eds.) Blackwell Scientific Publications, Oxford, 1985, p. 110) and a total span of 300–350 Å (Turner, M. W., et al., The *Plasma Proteins: An Introduction*, Pitman Medical & Scientific Publishing Co. Ltd., London, 1971, p. 22).

EXAMPLE 13

Immobilization of Penicillin Acylase onto Polymer Beads and Activity of teh Immobilized Enzyme Immobilization of an enzyme, namely, penicillin acylase, onto the polymer bead of the present invention was carried out conveniently using the hydroxyl-group-containing beads prepared, for example, in Examples 4 and 8 above. This involved the formation of an epoxy derivative of the polymer bead with epichlorohydrin under basic conditions, as described in paragraph A of Example 11 above. The epoxy activated polymer bead (250 mg) was thoroughly washed and then suspended in 2.5 mL of 0.1 M potassium phosphate buffer, pH 8.5 (coupling buffer), to which was added a 50 μL aliquot of penicillin acylase (EC 3.5.1.11) from *Escherichia coli* 5K (96.8 mg protein/mL, specific activity=4 U/mg by 6-nitro-3-(phenylacetamido)benzoic acid, NIPAB, assay), obtained from Braunschweiger Biotechnologie, Germany. This was mixed overnight (-16 h) at room temperature by end-over-end rotation on a hematology mixer.

The supernatant was removed and combined with a brief washing of the polymer beads with the said buffer to determine the residual protein and the enzyme activity recovered. The polymer bead with the immobilized enzyme was thoroughly washed with the coupling buffer containing 1 M NaCl to remove any noncovalently bound enzyme and/or protein, and then suspended in 0.05 M potassium phosphate buffer, pH 7.5 (assay buffer). Duplicate portions (50 mg each) of the suction-dried polymer bead were assayed in a Bio-rad mini-column to which was added 2 mL of the assay buffer and 0.8 mL of 3 mM NIPAB solution. This was mixed continuously and the difference between the products formed in 72 s and 102 s at 21° C., measured by absorbance at 405 nm and an extinction coefficient of 8.97 $cm^2/\mu mole$, was used to calculate the enzyme activity. Under the experimental conditions used, 4–5 mg protein/g of polymer bead (prepared by Example 4) which corresponds to 16–20 U of enzyme activity per gram of the bead was immobilized.

We claim:

1. A method to prepare crosslinked organic polymer rigid, porous beads, which method comprises polymerizing a suspension containing at least one monoethylenically unsaturated monomer and at least one polyethylenically unsaturated monomer in the presence of inorganic particles containing pores, which (inorganic particles have a diameter of at least 0.1 microns are preabsorbed with sufficient blowing agent to fill said pores, under conditions wherein said blowing agent is inert; followed by activating said preabsorbed blowing agent; followed by dissolution of said inorganic particles.

2. The method of claim 1, wherein said inorganic particles are porous silica or alumina.

3. The method of claim 1, wherein the blowing agent is a peroxide or an azoisonitrile.

4. The method of claim 1 wherein the monoethylenically monomer is styrene, an acrylic ester, a methacrylic ester, vinyl acetate, vinyl propionate or vinylbenzyl chloride.

5. The method of claim 1, wherein the polyethylenically unsaturated crosslinking monomer is divinyl benzene, triallyl isocyanurate or pentaerythritol trimethacrylate.

6. The method of claim 1, wherein the volume of blowing agent is substantially the same as the pore volume of said inorganic particles.

7. The method of claim 1, wherein said blowing agent is activated at elevated temperatures and said polymerization is conducted at a temperature below that at which the blowing agent is activated.

* * * * *